United States Patent
Sia

(10) Patent No.: US 9,724,469 B2
(45) Date of Patent: Aug. 8, 2017

(54) METHOD AND A SYSTEM FOR CONTROLLING DISCOMFORT LEVEL

(75) Inventor: Tiong Heng Alex Sia, Singapore (SG)

(73) Assignee: Singapore Health Services Pte. Ltd., Singapore (SG)

(*) Notice: Subject to any disclaimer, the term of this patent is extended or adjusted under 35 U.S.C. 154(b) by 32 days.

(21) Appl. No.: 14/006,898

(22) PCT Filed: Mar. 19, 2012

(86) PCT No.: PCT/SG2012/000090
§ 371 (c)(1),
(2), (4) Date: Dec. 3, 2013

(87) PCT Pub. No.: WO2012/128718
PCT Pub. Date: Sep. 27, 2012

(65) Prior Publication Data
US 2014/0081235 A1 Mar. 20, 2014

Related U.S. Application Data

(60) Provisional application No. 61/466,959, filed on Mar. 24, 2011.

(51) Int. Cl.
*A61M 5/172* (2006.01)
*A61M 5/142* (2006.01)

(52) U.S. Cl.
CPC .......... *A61M 5/1723* (2013.01); *A61M 5/142* (2013.01); *A61M 2230/04* (2013.01); *A61M 2230/30* (2013.01)

(58) Field of Classification Search
CPC .......... A61M 2230/04; A61M 2230/30; A61M 5/142; A61M 5/172; A61M 5/1723

USPC .............................. 604/500, 502–503, 65–66
See application file for complete search history.

(56) References Cited

U.S. PATENT DOCUMENTS

| | | | | |
|---|---|---|---|---|
| 5,069,668 A | * | 12/1991 | Boydman | A61M 5/172 604/121 |
| 2003/0135087 A1 | * | 7/2003 | Hickle | G06F 19/3406 600/26 |
| 2004/0103897 A1 | * | 6/2004 | Hickle | G06F 19/3468 128/204.23 |
| 2005/0177096 A1 | * | 8/2005 | Bollish et al. | 604/65 |

(Continued)

FOREIGN PATENT DOCUMENTS

| | | |
|---|---|---|
| CA | 2 275 530 A1 | 12/2000 |
| WO | 2004/060443 A2 | 7/2004 |

(Continued)

OTHER PUBLICATIONS

Hinova et al., "Systemic Remifentanil for Labor Analgesia," *Anesth Analg* 109(6): 1925-1929, Dec. 2009.

(Continued)

*Primary Examiner* — Quynh-Nhu H Vu
(74) *Attorney, Agent, or Firm* — Seed IP Law Group LLP

(57) ABSTRACT

Present invention relates to a method of controlling the discomfort level experienced by a subject. The method comprises receiving a signal from the subject to initiate comfort relief, determining vital sign data of the subject, determining whether the vital sign data fulfills a predetermined criterion, and performing an infusion regime of infusing a comfort relief drug into the subject based on whether the vital sign data fulfills the predetermined criterion.

14 Claims, 3 Drawing Sheets

(56) References Cited

U.S. PATENT DOCUMENTS

| | | | |
|---|---|---|---|
| 2007/0015972 A1* | 1/2007 | Wang | A61B 5/0484 |
| | | | 600/300 |
| 2007/0093786 A1 | 4/2007 | Goldsmith et al. | |
| 2007/0191817 A1* | 8/2007 | Martin | 604/890.1 |

FOREIGN PATENT DOCUMENTS

| | | |
|---|---|---|
| WO | 2005/056087 A1 | 6/2005 |
| WO | 2007/033025 A2 | 3/2007 |

OTHER PUBLICATIONS

Leong et al., "A Comparison Between Remifentanil and Meperidine for Labor Analgesia: A Systematic Review," *Anesth Analg 113*(4): 818-825, Oct. 2011.

Sia et al., "Computer-integrated patient-controlled epidural analgesia: a preliminary study on a novel approach of providing pain relief in labour," *Singapore Med J 47*(11): 951-956, 2006.

\* cited by examiner

METHOD AND A SYSTEM FOR CONTROLLING DISCOMFORT LEVEL

CROSS-REFERENCE TO RELATED APPLICATION

This application claims the benefit of priority of U.S. Provisional Patent Application No. 61/466,959, filed 24 Mar. 2011, the contents of which being hereby incorporated by reference in its entirety for all purposes.

TECHNICAL FIELD

The invention relates to a method and a system of controlling the discomfort level experienced by a subject, and in particular, to a patient-controlled method and system of controlling the discomfort level experienced by the subject.

BACKGROUND

Epidural analgesia has been established as the "gold standard" for pain relief in labor. However, there are many parturients who do not receive it either due to medical contraindications or personal refusal. As a corollary, there are many who are unwilling or uncomfortable with having an epidural needle inserted in their backs for fears of side effects and complications. Indeed, epidural analgesia may be unsuitable or contraindicated for some, including those with severe back problems. Epidural analgesia may also be deemed unsuitable for some who are in pain but may be in 'spurious' labor as well as those who are in late labor for which there might not be enough time for a fully effective epidural pain relief to be established. In some situations, an epidural may not be fully effective and some other modality of pain management may be required.

Currently, the other methods of providing pain relief involve principally the use of a gas mixture called entonox or an injection of an opioid into the muscle or vein. These methods have not been found to be effective apart from producing side effects. Similarly, epidural anesthesia during a cesarean section may require additional medication to render a greater quality of pain relief.

There have been some recent developments on the existing treatment options. For example, the use of intravenous (IV) remifentanil, a fast acting opioid that has seemingly minimal long term effects due to the favorable pharmacokinetic profile, has gained much popularity in the context of treatment for labor pain. Intravenous drugs could be administered via a patient-controlled modality, whereby the patient pushes a button to trigger the administration of drug intravenously when pain is felt by the patient (Sia et al., *Singapore Med* 1, 2006, 47, 951-956; Hinova et al., *Anesth Analg.*, 2009, 109, 1925-1929).

In recent years, patient-controlled analgesia (PCA) using the synthetic opioid remifentanil has been used with some success as an alternative to epidural analgesia, conferring moderate analgesia especially in early labor. As with other opioids, the use of remifentanil is also limited by known maternal side effects which include bradycardia, sedation and respiratory depression.

Despite the recent use of patient-controlled intravenous remifentanil administration which appears to be superior to many other modalities of treatment (Leong at al., *Anesth Analg.*, 2011, 113, 818-825) and is considered a good alternative to epidural analgesia, the optimal infusion regimen in this respect is still contentious. This is because labour pain is intermittent and it escalates as labour progresses. Therefore, the doses used would be correspondingly and incrementally larger as labour progresses. Moreover, there is often a lag time before the full effect of a particular dose effectively kicks in. The use of remifentanil is associated with the common side effects of opioids albeit transient due to its non-accumulative and rapid effect. However, some side effects, such as respiratory depression, would be sinister and should be prevented at all costs. Another potential side effect is the fetus' reaction to the drug which could manifest as an adverse fetal heart rate (slowing, a loss of reactivity or deceleration).

Therefore, there is a need to provide for a patient-controlled analgesia methodology with enhanced efficacy, safety and personalization of pain relief therapy with minimum side effects.

SUMMARY

According to a first aspect of the invention, there is provided a method of controlling the discomfort level experienced by a subject, comprising:
receiving a signal from the subject to initiate comfort relief;
determining vital sign data of the subject;
determining whether the vital sign data fulfils a predetermined criterion; and
performing an infusion regime of infusing a comfort relief drug into the subject based on whether the vital sign data fulfils the predetermined criterion.

According to another aspect, there is provided a system of controlling the discomfort level experienced by a subject, comprising:
a receiver configured to receive a signal from the subject to initiate comfort relief;
at least one monitor configured to determine vital sign data of the subject;
a determining circuit configured to determine whether the vital sign data fulfils a predetermined criterion;
at least one infusion device configured to infuse a comfort relief drug into the subject; and
a control unit configured to control the at least one infusion device to infuse the comfort relief drug into the subject, based on whether the vital sign data fulfils a predetermined criterion.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

DESCRIPTION

The following detailed description refers to the accompanying drawings that show, by way of illustration, specific details and embodiments in which the invention may be practised. These embodiments are described in sufficient detail to enable those skilled in the art to practise the invention. Other embodiments may be utilized and changes may be made without departing from the scope of the invention. The various embodiments are not necessarily mutually exclusive, as some embodiments can be combined with one or more other embodiments to form new embodiments.

The present invention offers an effective, safe and personalized therapy to alleviate, reduce, or control the discomfort level experienced by a subject. The subject or patient, as used interchangably hereinafter, may be experiencing discomfort, such as pain, irritation, and any other unpleasant suffering or sensation.

Figure 2:
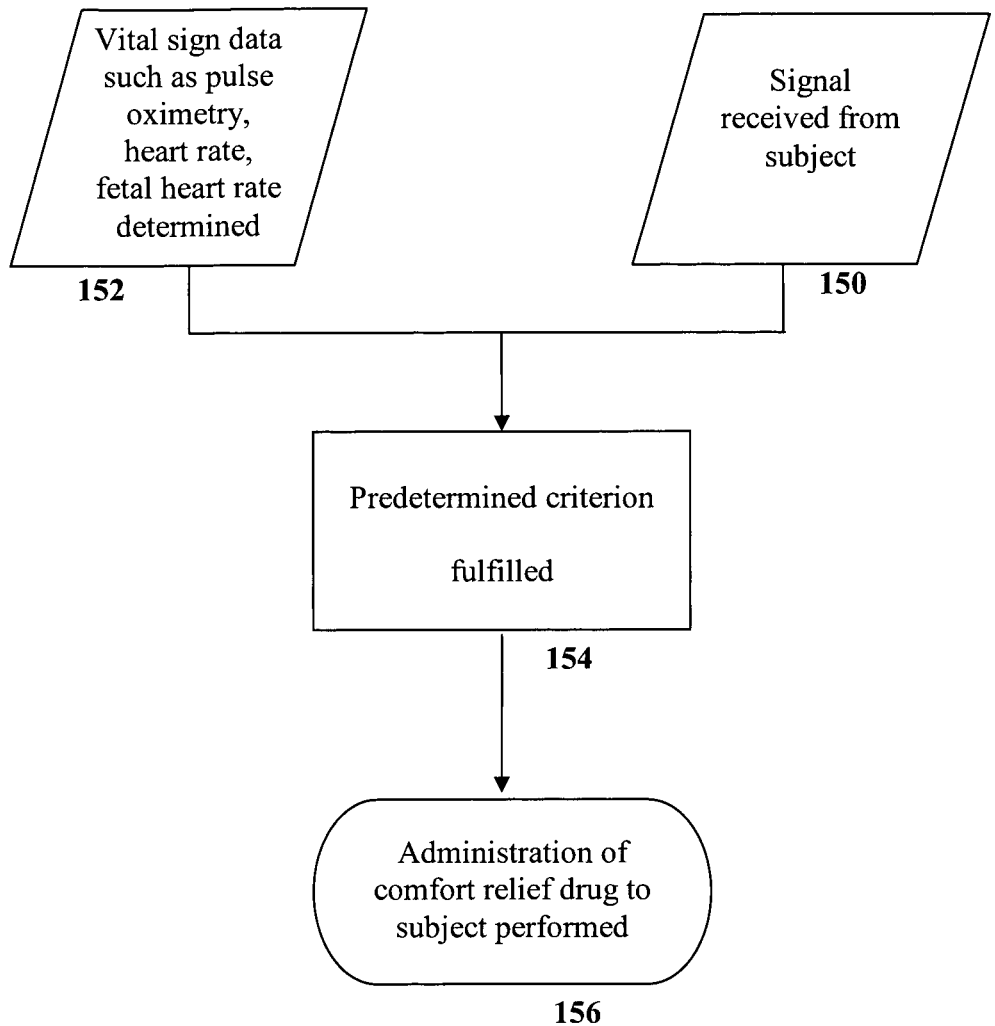
FIG. 2 shows a schematic illustration of the present method for controlling the discomfort level experienced by a subject.

In various embodiments as illustrated in FIG. 2, a method of controlling the discomfort level experienced by a subject is provided. The method may include receiving a signal from the subject to initiate comfort relief (150), determining vital sign data of the subject (152), determining whether the vital sign data fulfils a predetermined criterion (154), and performing an infusion regime of infusing a comfort relief drug into the subject based on whether the vital sign data fulfils the predetermined criterion (156).

In various embodiments, the method may also be provided for controlling the pain level experienced by a patient. In one embodiment, a method of controlling the pain level experienced by a subject is provided. The method may include receiving a signal from the subject to initiate pain relief, determining vital sign data of the subject, determining whether the vital sign data fulfils a predetermined criterion, and performing an infusion regime of infusing a pain relief drug into the subject based on whether the vital sign data fulfils the predetermined criterion.

In various embodiments, the comfort relief drug infused into the subject may be a pain relief drug or a sedative drug.

In one embodiment, the patient may be experiencing labour pain and may be infused with remifentanil to control the pain level.

Currently there is no established methodology or system that integrate critical parameters, i.e. vital sign data, into pain relief regimens. The ability to integrate critical parameters into the pain relief regimens is important as this would enable clinicians to be more aggressive in managing pain during labour without compromising on safety to the patients, thereby achieving an effective and safe pain relief therapy. This would also provide a reliable pain relief alternative to epidural administration.

As mentioned earlier, the use of epidural, though highly popular, is not without its attendant risks including lowering of blood pressure, numbness of legs, urinary retention, post procedural headache, and very rarely, nerve damage and other life threatening complications. Other treatment options, which do not involve a spinal or epidural injection, are ineffective and may be associated with other side effects (vide ante).

On the other hand, the present invention only requires an intravenous cannula, which all newly admitted patients to the labour ward would have been given upon admission. Pain relief drugs are then infused into the patients via the intravenous cannula without subjecting the patients to additional injections such as to the spine.

In various embodiments, the subject may send a signal to initiate comfort relief prior to experiencing the discomfort, or immediately upon experiencing the discomfort, or even after experiencing the discomfort. In certain embodiments, the subject may not send the signal immediately upon experiencing the discomfort and may choose to endure the discomfort until a point when the discomfort becomes unbearable before sending the signal.

The subject may send a signal to a receiver configured to receive the signal to initiate comfort relief. For example, the subject may send the signal by pressing a demand button acting as an interface between the subject and a control unit configured to perform the infusion regime of infusing the comfort relief drug into the subject.

In various embodiments, determining the vital sign data of the subject may include obtaining a pulse oximetry data indicating the oxygen concentration of the blood of the subject.

In one embodiment, the pulse oximetry data may be obtained by monitoring the oxygenation level of the subject's haemoglobin via a pulse oximeter.

In various embodiments, determining whether the vital sign data fulfils a predetermined criterion may include determining whether the obtained pulse oximetry data is above a predetermined threshold pulse oximetry value.

In various embodiments, the vital sign data is determined to fulfill a predetermined criterion when the obtained pulse oximetry data is above the predetermined threshold pulse oximetry value.

In various embodiments, the predetermined threshold pulse-oximetry value (SpO2) may be about 92% saturation.

In certain embodiments, the predetermined threshold pulse-oximetry value may be more than 92% saturation for a period of time. For example, the predetermined threshold pulse-oximetry value may be 93%, 94%, 95%, or 96% saturation.

In one embodiment, the predetermined threshold pulse-oximetry value may be about 95% saturation for a period of about 5 seconds.

In a further embodiment, the predetermined threshold pulse-oximetry value may be about 95% saturation for a period of about 10 seconds.

In a yet further embodiment, the predetermined threshold pulse-oximetry value may be about 95% saturation for a period of about 15 seconds.

In various embodiments, determining the vital sign data of the subject may further include obtaining a heart rate data indicating the heart rate of the subject.

In various embodiments, the heart rate data may be obtained by monitoring the heart rate of the subject via a heart rate monitor such as a wristwatch monitor.

In one embodiment, both the pulse oximetry data and the heart rate date may be monitored and obtained via a pulse oximeter.

In various embodiments, determining whether the vital sign data fulfils a predetermined criterion may include determining whether the obtained heart rate data is above a predetermined threshold heart rate value.

In various embodiments, the vital sign data is determined to fulfill a predetermined criterion when the obtained heart rate data is above the predetermined threshold heart rate value.

In various embodiments, the predetermined threshold heart rate value may be about 50 beats per minute.

In certain embodiments, the predetermined threshold heart rate value may be more than 50 beats per minute for a period of time. For example, the predetermined threshold heart rate value may be 55, 60, or 65 beats per minute.

In one embodiment, the predetermined threshold heart rate value may be about 60 beats per minute for a period of about 5 seconds.

In a further embodiment, the predetermined threshold heart rate value may be about 60 beats per minute for a period of about 10 seconds.

In a yet further embodiment, the predetermined threshold heart rate value may be about 60 beats per minute for a period of about 15 seconds.

In various embodiments, the heart rate data may further include a fetal heart rate data indicating the heart rate of a fetal carried by the subject.

In various embodiments, the fetal heart rate data may be obtained by monitoring the heart rate of the fetal carried by the subject via a Doppler fetal heart rate monitor.

In various embodiments, the predetermined threshold heart rate value may further include a predetermined threshold fetal heart rate value.

In various embodiments, determining whether the vital sign data fulfils a predetermined criterion may include determining whether the obtained fetal heart rate data is above a predetermined threshold fetal heart rate value.

In various embodiments, the vital sign data is determined to fulfill a predetermined criterion when the obtained fetal heart rate data is above the predetermined threshold fetal heart rate value.

In various embodiments, the predetermined threshold fetal heart rate value may be about 90 beats per minute.

In certain embodiments, the predetermined threshold fetal heart rate value may be more than 90 beats per minute for a period of time. For example, the predetermined threshold fetal heart rate value may be 95, 100, or 105 beats per minute.

In one embodiment, the predetermined threshold fetal heart rate value may be about 100 beats per minute for a period of about 5 seconds.

In a further embodiment, the predetermined threshold fetal heart rate value may be about 100 beats per minute for a period of about 10 seconds.

In various embodiments, the predetermined threshold fetal heart rate value may be about 100 beats per minute for a period of about 15 seconds.

In various embodiments, the infusion regime of infusing the comfort relief drug into the subject may be performed if the vital sign data fulfils the predetermined criterion.

In one embodiment, the infusion regime of infusing the comfort relief drug into the subject is performed when the vital sign data is above the predetermined threshold value of the vital sign data.

In various embodiments, the infusion regime may include controlling an infusion device to infuse a pain relief drug into the subject. For example, the infusion device may be a pump, intravenous drip, or a drip set.

In one embodiment, the infusion device may be a pump.

In various embodiments, the infusion device may be adapted to infuse a comfort relief drug of a different loading into the subject.

In various embodiments, the infusion device may be controlled to infuse the comfort relief drug of a first loading into the subject if the subject sends a first signal to initiate the comfort relief. In various embodiments, the first loading may include a bolus of 20 mic.

In various embodiments, the infusion device may be controlled to infuse the comfort relief drug of a second loading into the subject if the subject sends a second signal to initiate the comfort relief after having been infused with the first loading. In various embodiments, the second loading may include a bolus of 30 mic.

In various embodiments, the infusion device may be controlled to infuse the comfort relief drug of a third loading into the subject if the subject sends a third signal to initiate the comfort relief after having been infused with the second loading. In various embodiments, the third loading may include a bolus of 40 mic.

In various embodiments, the infusion regime may include the infusion of further loadings into the subject if deemed appropriate by the clinicians. Alternatively or additionally, the infusion regime may include a continuous infusion of a limit loading into the subject.

In various embodiments, the infusion device may be controlled to infuse the comfort relief drug of a fourth loading into the subject if the subject sends a fourth signal to initiate the comfort relief after having been infused with the third loading. In various embodiments, the fourth loading may include a bolus of 50 mic.

In various embodiments, the infusion device may be controlled to infuse the comfort relief drug of a limit loading at a continuous infusion rate into the subject if the subject sends a fifth signal to initiate the comfort relief. In various embodiments, the limit loading may include a bolus of 50 mic continuously infused at 0.025 mic/kg/min.

In various embodiments, the infusion device may be controlled to infuse the comfort relief drug of a limit loading at a continuous infusion rate into the subject if the subject sends a sixth signal to initiate the comfort relief. In various embodiments, the limit loading may include a bolus of 50 mic continuously infused at 0.05 mic/kg/min.

In various embodiments, the infusion device may be controlled to infuse the comfort relief drug of the limit loading at a continuous infusion rate into the subject if the subject sends a seventh signal to initiate the comfort relief. In various embodiments, the limit loading may include a bolus of 50 mic continuously infused at 0.075 mic/kg/min.

In various embodiments, the infusion device may be controlled to infuse the comfort relief drug of the limit loading at a continuous infusion rate into the subject if the subject sends an eighth signal to initiate the comfort relief. In various embodiments, the limit loading may include a bolus of 50 mic continuously infused at 0.1 mic/kg/min.

In various embodiments, the infusion regime may include controlling a plurality of infusion devices to infuse comfort relief drugs into the subject. For example, each of the plurality of infusion devices may be adapted to infuse a comfort relief drug of a different loading into the subject.

In various embodiments, a first infusion device of the plurality of infusion devices may be controlled to infuse the comfort relief drug of a first loading into the subject if the subject sends a first signal to initiate the comfort relief. In various embodiments, the first loading may include a bolus of 20 mic.

In various embodiments, a second infusion device of the plurality of infusion devices may be controlled to infuse the comfort relief drug of a second loading into the subject if the subject sends a second signal to initiate the comfort relief after having been infused with the first loading. In various embodiments, the second loading may include a bolus of 30 mic.

In various embodiments, a third infusion device of the plurality of infusion devices may be controlled to infuse the comfort relief drug of a third loading into the subject if the subject sends a third signal to initiate the comfort relief after having been infused with the second loading. In various embodiments, the third loading may include a bolus of 40 mic.

In various embodiments, a fourth infusion device of the plurality of infusion devices may be controlled to infuse the comfort relief drug of a fourth loading into the subject if the subject sends a fourth signal to initiate the comfort relief after having been infused with the third loading. In various embodiments, the fourth loading may include a bolus of 50 mic.

In various embodiments, a fifth infusion device of the plurality of infusion devices may be controlled to infuse the comfort relief drug of a limit loading at a continuous infusion rate into the subject if the subject sends a fifth signal to initiate the comfort relief. In various embodiments, the limit loading may include a bolus of 50 mic continuously infused at 0.025 mic/kg/min.

In various embodiments, a sixth infusion device of the plurality of infusion devices may be controlled to infuse the comfort relief drug of a limit loading at a continuous infusion rate into the subject if the subject sends a sixth signal to initiate the comfort relief. In various embodiments, the limit loading may include a bolus of 50 mic continuously infused at 0.05 mic/kg/min.

In various embodiments, a seventh infusion device of the plurality of infusion devices may be controlled to infuse the comfort relief drug of the limit loading at a continuous infusion rate into the subject if the subject sends a seventh signal to initiate the comfort relief. In various embodiments, the limit loading may include a bolus of 50 mic continuously infused at 0.075 mic/kg/min.

In various embodiments, an eighth infusion device of the plurality of infusion devices may be controlled to infuse the comfort relief drug of the limit loading at a continuous infusion rate into the subject if the subject sends an eighth signal to initiate the comfort relief. In various embodiments, the limit loading may include a bolus of 50 mic continuously infused at 0.1 mic/kg/min.

In alternative embodiments, the infusion device may be adapted to include a plurality of infusion lines to infuse the comfort relief drugs of different loadings into the subject.

Various embodiments of a second aspect of the present invention provide for a system of controlling the discomfort level experienced by a subject. The system may include a receiver configured to receive a signal from the subject to initiate comfort relief, at least one monitor configured to determine vital sign data of the subject, a determining circuit configured to determine whether the vital sign data fulfils a predetermined criterion, at least one infusion device configured to infuse a comfort relief drug into the subject, and a control unit configured to control the at least one infusion device to infuse the comfort relief drugs into the subject, based on whether the vital sign data fulfils a predetermined criterion.

Various embodiments also provide for a system of controlling the pain level experienced by a subject. The system may include a receiver configured to receive a signal from the subject to initiate pain relief, at least one monitor configured to determine vital sign data of the subject, a determining circuit configured to determine whether the vital sign data fulfils a predetermined criterion, at least one pump configured to infuse a pain relief drug into the subject, and a control unit configured to control the at least one pump to infuse the pain relief drugs into the subject, based on whether the vital sign data fulfils a predetermined criterion.

In various embodiments, the at least one monitor configured to determine vital sign data of the subject may include a pulse oximeter for obtaining pulse oximetry data indicating the oxygen concentration of the blood of the subject.

In various embodiments, the at least one infusion device may be configured to infuse a comfort relief drug based on whether the obtained pulse oximetry data is above a predetermined threshold pulse oximetry value.

In one embodiment, the at least one infusion device may be configured to infuse a comfort relief drug when the obtained pulse oximetry data is above a predetermined threshold pulse oximetry value.

In various embodiments, the at least one monitor configured to determine vital sign data of the subject may include a heart rate monitor for obtaining heart rate data indicating the heart rate of the subject.

In various embodiments, the infusion device may be configured to infuse a comfort relief drug based on whether the obtained heart rate data is above a predetermined threshold heart rate value.

In one embodiment, the at least one infusion device may be configured to infuse a comfort relief drug when the obtained heart rate data is above a predetermined threshold heart rate value.

In various embodiments, the heart rate data may further include a fetal heart rate data indicating the heart rate of a fetal carried by the subject.

In various embodiments, the predetermined threshold heart rate value may further include a predetermined threshold fetal heart rate value.

In various embodiments, the predetermined threshold value of the respective vital sign data may be defined as above.

In various embodiments, the at least one infusion device may be configured to infuse the comfort relief drug if the vital sign data fulfils a predetermined criterion. For example, the at least one infusion device may be a pump, intravenous drip, or a drip set.

In one embodiment, the at least one infusion device may be a pump.

In various embodiments, the at least one infusion device may be adapted to infuse a comfort relief drug of a different loading into the subject.

In various embodiments, the control unit may be configured to control the at least one infusion device to infuse the comfort relief drug of a first loading into the subject if the subject sends a first signal to initiate the comfort relief. In various embodiments, the first loading may include a bolus of 20 mic.

In various embodiments, the control unit may be adapted to control the at least one infusion device to infuse the comfort relief drug of a second loading into the subject if the subject sends a second signal to initiate the comfort relief after having been infused with the first loading. In various embodiments, the second loading may include a bolus of 30 mic.

In various embodiments, the control unit may be adapted to control the at least one infusion device to infuse the comfort relief drug of a third loading into the subject if the subject sends a third signal to initiate the comfort relief after having been infused with the second loading. In various embodiments, the third loading may include a bolus of 40 mic.

In various embodiments, the control unit may be adapted to control the at least one infusion device to infuse the comfort relief drug of a fourth loading into the subject if the subject sends a fourth signal to initiate the comfort relief after having been infused with the third loading. In various embodiments, the fourth loading may include a bolus of 50 mic.

In various embodiments, the control unit may be adapted to control the at least one infusion device to infuse the comfort relief drug of a limit loading at a continuous infusion rate into the subject if the subject sends a fifth signal to initiate the comfort relief. In various embodiments, the limit loading may include a bolus of 50 mic continuously infused at 0.025 mic/kg/min.

In various embodiments, the control unit may be adapted to control the at least one infusion device to infuse the comfort relief drug of a limit loading at a continuous infusion rate into the subject if the subject sends a sixth signal to initiate the comfort relief. In various embodiments, the limit loading may include a bolus of 50 mic continuously infused at 0.05 mic/kg/min.

In various embodiments, the control unit may be adapted to control the at least one infusion device to infuse the comfort relief drug of the limit loading at a continuous infusion rate into the subject if the subject sends a seventh signal to initiate the comfort relief. In various embodiments, the limit loading may include a bolus of 50 mic continuously infused at 0.075 mic/kg/min.

In various embodiments, the control unit may be adapted to control the at least one infusion device to infuse the comfort relief drug of the limit loading at a continuous infusion rate into the subject if the subject sends an eighth signal to initiate the comfort relief. In various embodiments, the limit loading may include a bolus of 50 mic continuously infused at 0.1 mic/kg/min.

In various embodiments, the at least one infusion device may include a plurality of infusion devices.

In various embodiments, the control unit may be adapted to control a first infusion device of the plurality of infusion devices to infuse the comfort relief drug of a first loading into the subject if the subject sends a first signal to initiate the comfort relief. In various embodiments, the first loading may include a bolus of 20 mic.

In various embodiments, the control unit may be adapted to control a second infusion device of the plurality of infusion devices to infuse the comfort relief drug of a second loading into the subject if the subject sends a second signal to initiate the comfort relief after having been infused with the first loading. In various embodiments, the second loading may include a bolus of 30 mic.

In various embodiments, the control unit may be adapted to control a third infusion device of the plurality of infusion devices to infuse the comfort relief drug of a third loading into the subject if the subject sends a third signal to initiate the comfort relief after having been infused with the second loading. In various embodiments, the third loading may include a bolus of 40 mic.

In various embodiments, the control unit may be adapted to control a fourth infusion device of the plurality of infusion devices to infuse the comfort relief drug of a fourth loading into the subject if the subject sends a fourth signal to initiate the comfort relief after having been infused with the third loading. In various embodiments, the fourth loading may include a bolus of 50 mic.

In various embodiments, the control unit may be adapted to control a fifth infusion device of the plurality of infusion devices to infuse the comfort relief drug of a limit loading at a continuous infusion rate into the subject if the subject sends a fifth signal to initiate the comfort relief. In various embodiments, the limit loading may include a bolus of 50 mic continuously infused at 0.025 mic/kg/min.

In various embodiments, the control unit may be adapted to control a sixth infusion device of the plurality of infusion devices to infuse the comfort relief drug of a limit loading at a continuous infusion rate into the subject if the subject sends a sixth signal to initiate the comfort relief. In various embodiments, the limit loading may include a bolus of 50 mic continuously infused at 0.05 mic/kg/min.

In various embodiments, the control unit may be adapted to control a seventh infusion device of the plurality of infusion devices to infuse the comfort relief drug of the limit loading at a continuous infusion rate into the subject if the subject sends a seventh signal to initiate the comfort relief. In various embodiments, the limit loading may include a bolus of 50 mic continuously infused at 0.075 mic/kg/min.

In various embodiments, the control unit may be adapted to control an eighth infusion device of the plurality of infusion devices to infuse the comfort relief drug of the limit loading at a continuous infusion rate into the subject if the subject sends an eighth signal to initiate the comfort relief. In various embodiments, the limit loading may include a bolus of 50 mic continuously infused at 0.1 mic/kg/min.

In alternative embodiments, the at least one infusion device may be adapted to include a plurality of infusion lines to infuse the comfort relief drugs of different loadings into the subject.

With the present invention, patients' need for comfort relief may be customised and responded to for each individual patient. In an exemplary embodiment, the present system would study the pattern of analgesic use in 15 min epochs and make the decision to differ (usually increase) the demand doses or initiate a continuous infusion to maintain the plasma level of remifentanil that would be appropriate for the degree of pain felt. An external detector of uterine activity would be incorporated to capture data on uterine activity. An integration of the reading of pulse oximetry values (e.g. from a reliable probe, such as a ring LED or 'reflectance' sticker on the skin) to ensure that it is not lower than 94% saturation and to ensure that the administration of analgesics is modulated by fetal heart recordings (with the option of termination if the heart rate is less below 100 beats per minute or if the pattern is non-reassuring) would enhance the efficacy of the present method and more importantly, safety and comfort of the patient.

Therefore, with the incorporation of vital signs data reading as part of the present methodology, the present invention affords a much safer alternative to existing patient-controlled intravenous analgesia system. Compared to the existing industry gold standard of administering epidural to offer pain relief, the present method not only obviates the need for the insertion of the epidural needle and its attendant problems, it also provides a better opportunity for individualization of therapy within the safety limits inherent in the invention.

The present inventive concept can be extended to other perioperative, post operative pain as well as chronic pain setups.

In order that the invention may be readily understood and put into practical effect, particular embodiments will now be described by way of the following non-limiting examples.

EXAMPLES

Example 1: Implementation of Methodolody

Figure 1A:
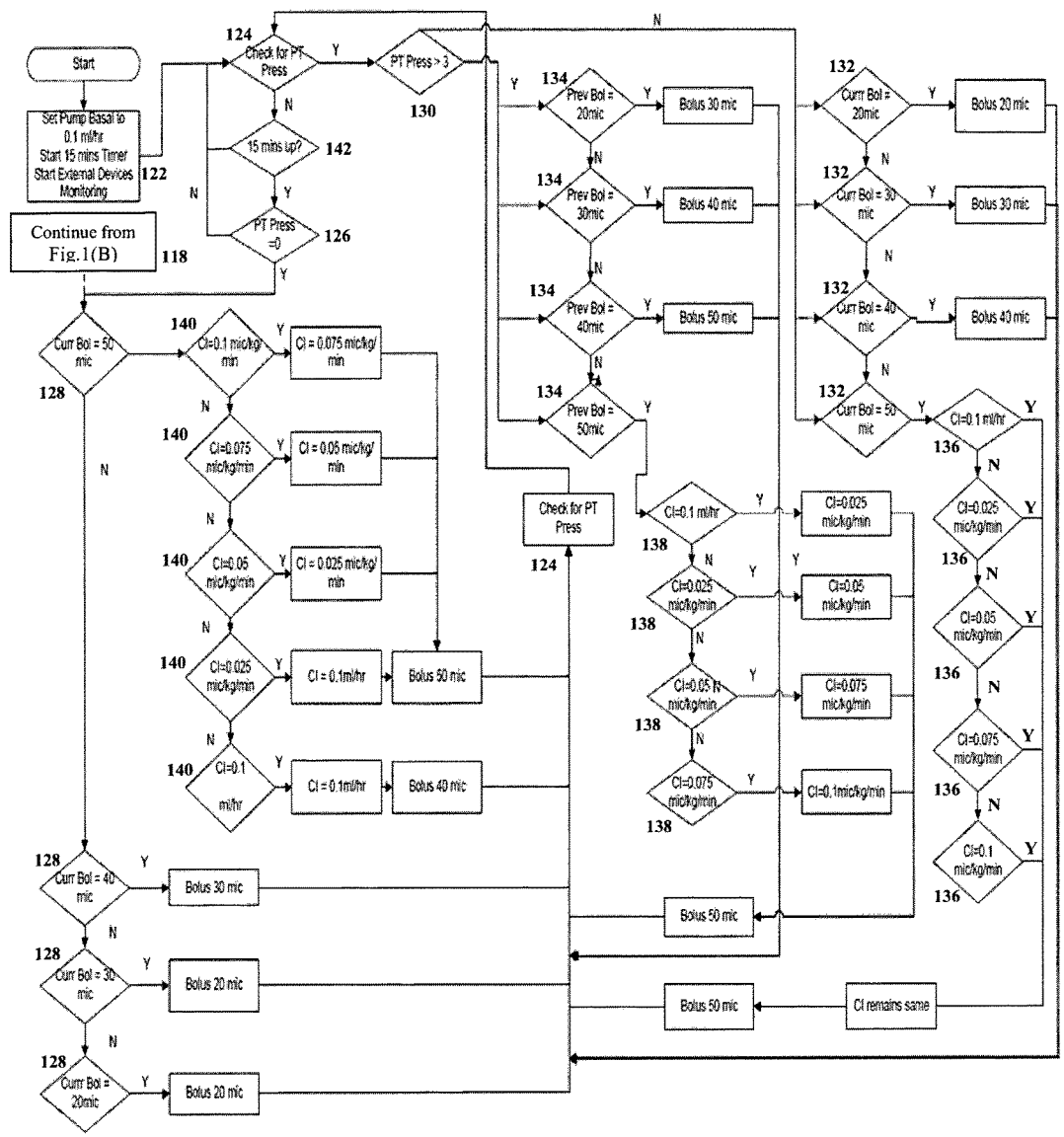
FIG. 1 illustrates the algorithm for implementing the present methodology; (A) outlines the computer algorithm for infusing remifentanil upon receiving a signal from a patient to initiate the pain relief; (B) outlines the monitoring and obtaining of pulse-oximetry data (pulse rate and oxygen concentration of the blood) and fetal heart rate to stop the infusion pump in the event that these parameters are outside the predetermined limits or criteria.
Figure 1B:
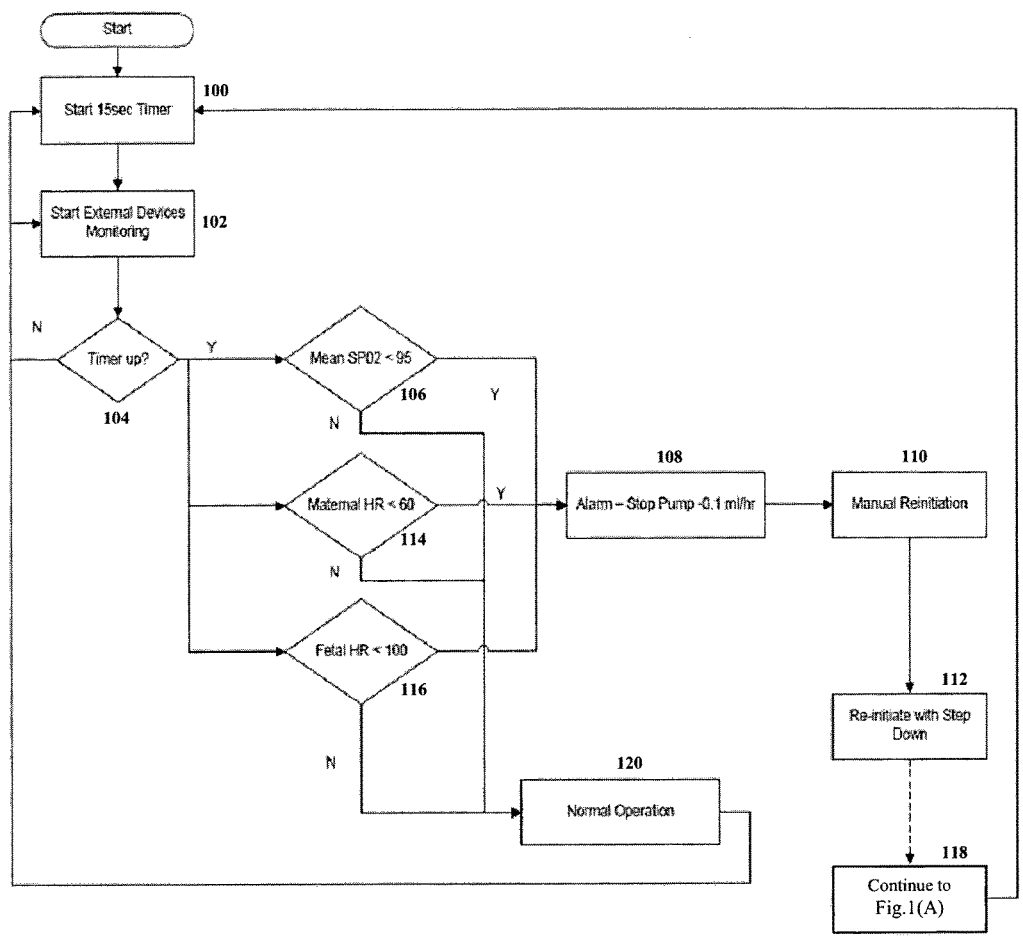

Generally, FIGS. 1(A) and 1(B) illustrates an algorithm for implementing the present methodology of vital signs-controlled, patient-assisted intravenous analgesia using remifentanil.

Specifically, FIG. 1(A) outlines the computer algorithm for infusing remifentanil upon receiving a signal from a patient to initiate the pain relief while FIG. 1(B) outlines the monitoring and obtaining of pulse-oximetry data (pulse rate and oxygen concentration of the blood) and fetal heart rate to stop the infusion pump in the event that these parameters are outside the predetermined limits or criteria.

The syringe pump initially contains about 50 ml of remifentanil to be diluted to form a reservoir of the drug to relieve pain. The patient is given a patient-controlled activation button to self inject drugs by sending a signal to the system to deliver pain relief medication from the reservoir. The input from this would also capture data related to patients' changing needs so as to help hone efficacy and individualization of therapy.

Vital signs data obtained for pulse-oximetry, pulse rate and fetal heart rate would dictate when to stop and manually re-initiate the pain relief therapy. If any one of these data does not meet safety limits predetermined by the clinicians, the infusion regimen will be halted.

Briefly, as shown in FIG. 1(B), at the "Start" step, a 15-second timer is activated (100). Vital signs monitors are simultaneously activated (102). Vital signs data are then monitored, obtained, and compared with a predetermined criterion after the 15-second period is up (104). If the obtained vital signs data are above the predetermined criterion, the regime will continue with an increase in the dose level (i.e. a step up) as illustrated in FIG. 1(A) to be described later. In this example, the vital signs data include pulse oximetry $SpO_2$, maternal heart rate, and fetal heart rate.

The predetermined threshold pulse oximetry $SpO_2$ value is 95. If the pulse oximetry $SpO_2$ is below 95 for about 15 seconds (106), an alarm will be triggered and the regimen is halted (108). Manual re-initiation has to be activated (110). The regime is re-initiated with one step down, i.e. a step down of the dose level (112). The step down regime (118) is illustrated in FIG. 1(A) to be described later.

The predetermined threshold maternal heart rate value is 60. If the maternal heart rate is less than 60 for about 15 seconds (114), an alarm will be triggered and the regime is halted (108). Manual re-initiation has to be activated (110). The regime is re-initiated with one step down, i.e. a step down of the dose level (112). The step down regime (118) is illustrated in FIG. 1(A) to be described later.

The predetermined threshold fetal heart rate value is 100. If the fetal heart rate is less than 100 for about 15 seconds (116), an alarm will be triggered and the regime is halted (108). Manual re-initiation has to be activated (110). The regime is re-initiated with one step down, i.e. a step down of the dose level (112). The step down regime (118) is illustrated in FIG. 1(A) to be described later.

At the same time of activating the 15-second timer (100) and vital signs monitors (102), a 15-minute timer (122) is also activated. If all obtained vital signs data are above the respective predetermined threshold value, normal operation of the regime will be carried out. The step up regime illustrated in FIG. 1(A) is briefly described as follows.

During the 15-minute interval, the system will continuously check whether a signal has been sent from the patient (124). If after the 15-minute interval (142) no signal has been received (126), the system will check the current bolus level. If the patient has not previously been infused with the drug, the current bolus level will be set at the minimum bolus, in this case, 20 mic (128). Thereafter, the system will continue to check whether a signal has been sent from the patient (124).

When the system receives a signal, it will check whether a signal has been received previously (130) and whether the 15-minute interval since the receipt of the last signal has lapsed. If 3 or less signals have been received within the same 15-minute interval, the system proceeds to check the current bolus level (132). In the case where the current bolus is 20 mic, then the system will maintain infusion at 20 mic without lockout and the vital signs are monitored for the next 15 minutes. Thereafter, the system will continue to check whether a signal has been sent from the patient (124). If a further signal is received within the same 15-minute interval and the total number of signals received during this 15-minute interval is still not more than 3 (130), the system proceeds to check the current bolus level (132) and infuse the corresponding bolus. For example, if step-up has been carried out earlier and the current bolus level is 40 mic, then a bolus of 40 mic will be infused. This maintenance regime will continue so long as 3 or less signals are received within the same 15-minute interval.

On the other hand, if the further signal is received within the same 15-minute interval and the total number of signals received during this 15-minute interval is 4 or greater (130), a step-up bolus level will be infused. For example, the system checks the that the previous bolus level (134) was 20 mic and infuses the corresponding bolus of a higher level of 30 mic. The vital signs are monitored for the next 15 minutes and the system will continue to check whether a signal has been sent from the patient (124). This step-up regime will continue so long as 4 or greater signals are received during the same 15-minute interval.

In both the maintenance regime and step-up regime, a limit loading of 50 mic has been set. In the maintenance regime, if the current bolus is the limit bolus level (132), subsequent receipt of signals will trigger continuous infusion of the drug at rates in accordance to that shown in FIG. 1(A) depending on the last continuous infusion rate (136). In this case, the continuous infusion rate will maintain at the last continuous infusion rate. In the step-up regime, if the previous bolus is the limit bolus level (134), subsequent receipt of signals will trigger continuous infusion of the drug at rates in accordance to that shown in FIG. 1(A) depending on the last continuous infusion rate (138). In this case, the continuous infusion rate will increase from the last continuous infusion rate.

For the stepping down regime, the step down dose, including continuous infusion rate, and monitor period is reversely carried out. The step-down regime will be implemented if a first signal is received after a 15-minute interval. If re-initiation with a step-down is triggered ((112), FIG. 1(B)), then the system will check the current bolus level (128). As illustrated in FIG. 1(A), if the current bolus is 40 mic, then the drug dose will be reduced and a bolus of 30 mic will be infused and the system continues to check for receipts of signals and monitoring of vital signs.

Similar to the step-up regime, the limit bolus level for the step-down regime is set at 50 mic (128). During the step-down, if the bolus is at the limit loading, then the current continuous infusion rate is determined (140). The continuous infusion rate will decrease in accordance with the rates and the bolus level illustrated in FIG. 1(A).

Example 2: Case Study

Example 2 is a case study of the methodology described in Example 1.

This example studies the parturient's pattern of analgesic use in 15 min epochs and titrate the demand doses and basal infusion rate to maintain a plasma level of remifentanil that is appropriate for the degree of pain felt. Continuous maternal pulse oximetry and heart rate values are integrated to temporarily stop the pumps and step down doses accordingly when predefined critical values are reached.

The programming of the regimen is set as follows: Lockout time 1 minute, pump automatically pauses for 5 minutes when $SpO_2$ reading falls below 92% for more than 15 seconds or when maternal HR falls below 50 for more than 15 seconds.

Parturients who initially declined epidural analgesia or who had contraindications to central neuraxial blockade were counseled upon arrival in the Delivery Suite at the Singapore's Kandang Kerbau Women's & Children's Hospital about the various pain relief alternatives available. Parturients who gave informed consent to use remifentanil therapy and were recruited into the case series were managed with a standardized protocol. Upon admission to the Delivery Suite, all patients had mandatory intravenous (IV) access established and baseline non-invasive arterial BP and HR recorded. Hydration with Lactated Ringer's solution was initiated at a rate of 80 ml/hr. Remifentanil was diluted into a concentration of 40 mcg/ml and the vital signs-controlled, patient-assisted intravenous analgesia (VPIA) regimen was started.

Remifentanil was administered via an intravenous infusion line with an anti-reflux valve to ensure precise drug administration and no backflow. All patients received supplemental oxygen at 4l/min via oxygen facemask and were written up for antiemetic therapy (intravenous metoclopromide 8 hourly prn). All patients were shown the proper use of the VPIA pump, and encouraged to press the demand button either at the beginning of a contraction or whenever a contraction was anticipated.

Maternal monitoring included non-invasive arterial blood pressure (BP), heart rate (HR) and respiratory rate (RR) taken at regular intervals, and continuous pulse oximetry (SpO2). Continuous FHR and uterine activity were recorded using external cardiotocograph monitoring. Any complications arising from remifentanil analgesic therapy were reported to the anesthetist on-duty immediately and the patient would be attended to promptly. In the event of inadequate labour analgesia using remifentanil, the study participants could decide to have epidural analgesia instead, or request for cesarean section if necessary.

Results

The outcomes of interest incorporate both efficacy and safety endpoints, including hourly maternal pain score profiles (0-100 Visual Analog Scale (VAS)), incidence of maternal side effects such as sedation, respiratory depression, oxygen desaturation less than 95%, bradycardia with heart rate less than 60 beats per minute, pruritus, nausea and vomiting. Total and hourly remifentanil consumption are studied, together with obstetric and neonatal outcomes. 24 hours post-delivery, an overall satisfaction score (0-100) with analgesic therapy were sought from the parturients.

Data from five parturients were collected between 31 Jan. 2012 to 3 Mar. 2012.

All 5 parturients reported high VAS of 9-10 before remifentanil therapy was initiated.

A moderate reduction of labour pain from VAS of 9-10 to 3-7 was achieved during the duration of labour. Four out of the five parturients used inhaled Entonox to supplement analgesia during delivery when more intense pain recurred.

All parturients had transient episodes (median 3, maximum-minimum 2-21) of oxygen saturation of 92% that automatically stopped the VPIA pump. These episodes recovered quickly allowing the VPIA pump to be restarted after 5 minutes. But all five parturients had mean hourly SpO2 readings of at least 95% while on supplemental oxygen, suggesting that these transient episodes may not have had any clinical impact. This also demonstrated the importance of continuously monitoring the HR and SpO2 of patients who are receiving parenteral opioids for pain relief in this setting. Only 1 patient had HR of 50 with automatic pause of the VPIA pump, but with no associated hypotension. None of the parturients demonstrated over-sedation as evidenced by a sedation score of more than 2. There were no maternal complaints of nausea or vomiting.

The patients received 95-515 mcg/hr of remifentanil (median 442); the median maternal satisfaction was 70 (maximum-minimum 50-90).

There were no episodes of fetal bradycardia or non-reassuring CTG requiring obstetrician intervention during remifentanil therapy. All neonates were vigorous at birth with 1 and 5 minute Apgars of 9. All the neonates had umbilical artery & vein cord pH of more than 7.2.

CONCLUSION

The VPIA regimen revolutionizes the management of labour pain using systemic opioids in women who are unable to receive epidural analgesia. Utilizing a three-pronged approach, the most important issues of efficacy, safety and personalization of opioidanalgesia for women in labour were addressed. The incorporation of vital signs readings into the auto-feedback loop driving the analgesic regimen promises to protect the well-being of both mother and baby. The automatic titration of analgesia according to maternal requirements may allow customization of therapy to match the unpredictable and dynamic nature of labour pain.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numberical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

The invention claimed is:

1. A method of controlling the discomfort level experienced by a subject, comprising: receiving a signal from the subject to initiate comfort relief; determining vital sign data of the subject; determining whether the vital sign data fulfils a predetermined criterion; and performing an infusion regime of infusing a comfort relief drug into the subject based on whether the vital sign data fulfils the predetermined criterion, wherein the infusion regime comprises controlling one or a plurality of infusion devices to infuse one or a plurality of comfort relief drugs into the subject, wherein each of the one or a plurality of infusion devices is adapted to infuse a comfort relief drug of one or a plurality of different loadings into the subject, wherein at least one infusion device is controlled to infuse the comfort relief drug of a first loading into the subject if the subject sends a first signal to initiate the comfort relief, wherein at least one infusion device is controlled to infuse the comfort relief drug of a second loading into the subject if the subject sends a second signal to initiate the comfort relief after having been infused with the first loading within a pre-determined period, wherein at least one infusion device is controlled to infuse the comfort relief drug of a third loading into the subject if the subject sends a third signal to initiate the comfort relief after having been infused with the second loading within the pre-determined period, wherein the third loading comprises a loading higher than the second loading and the second loading comprises a loading higher than the first loading, wherein each of the one or a plurality of infusion devices is controlled to infuse the comfort relief drug of a limit loading at a continuous infusion rate into the subject if the subject sends a further signal to initiate the comfort relief.

2. The method of claim 1, wherein determining the vital sign data of the subject comprises obtaining a pulse oximetry data indicating the oxygen concentration of the blood of the subject.

3. The method of claim 2, wherein determining whether the vital sign data fulfils a predetermined criterion comprises determining whether the obtained pulse oximetry data is above a predetermined threshold pulse oximetry value.

4. The method of claim 1, wherein determining the vital sign data of the subject comprises obtaining a heart rate data indicating the heart rate of the subject.

5. The method of claim 4, wherein determining whether the vital sign data fulfils a predetermined criterion comprises determining whether the obtained heart rate data is above a predetermined threshold heart rate value.

6. The method of claim 4, wherein the heart rate data further comprises a fetal heart rate data indicating the heart rate of a fetal carried by the subject.

7. The method of claim 6, wherein the predetermined threshold heart rate value further comprises a predetermined threshold fetal heart rate value.

8. The method of claim 1, wherein the infusion regime of infusing the comfort relief drug into the subject is performed if the vital sign data fulfils the predetermined criterion.

9. The method of claim 1, wherein each of the plurality of infusion devices is adapted to infuse a comfort relief drug of a different loading into the subject.

10. The method of claim 1, wherein if on expiry of the pre-determined period the patient has not been infused with a further loading since the first loading of the comfort relief drug then the bolus level is set at a minimum bolus.

11. A system of controlling the discomfort level experienced by a subject, comprising: a receiver configured to receive a signal from the subject to initiate comfort relief; at least one monitor configured to determine vital sign data of the subject; a determining circuit configured to determine whether the vital sign data fulfils a predetermined criterion; at least one infusion device configured to infuse a comfort relief drug into the subject; and a control unit configured to control the at least one infusion device to infuse the comfort relief drug into the subject, based on whether the vital sign data fulfils a predetermined criterion, wherein the control unit is configured to control the at least one infusion device to infuse the comfort relief drug of a first loading into the subject if the subject sends a first signal to initiate the comfort relief, wherein the control unit is adapted to control the at least one infusion device to infuse the comfort relief drug of a second loading into the subject if the subject sends a second signal to initiate the comfort relief after having been infused with the first loading within a pre-determined period, and wherein the control unit is adapted to control the at least one infusion device to infuse the comfort relief drug of a third loading into the subject if the subject sends a third signal to initiate the comfort relief after having been infused with the second loading within the pre-determined period, wherein the third loading comprises a loading higher than the second loading and the second loading comprises a loading higher than the first loading, wherein each of the one or a plurality of infusion devices is controlled to infuse the comfort relief drug of a limit loading at a continuous infusion rate into the subject if (i) the subject sends a further signal to initiate the comfort relief or (ii) if on expiry of the pre-determined period if no further signal is sent.

12. The system of claim 11, wherein the control unit is adapted to control the at least one infusion device to infuse the comfort relief drug of a limit loading at a continuous infusion rate into the subject if the subject sends a further signal to initiate the comfort relief.

13. The system of claim 11, wherein the at least one infusion device comprises a plurality of infusion devices.

14. The system of claim 13, wherein each of the plurality of infusion devices is adapted to infuse a comfort relief drug of a different loading into the subject.

* * * * *